United States Patent [19]

Hamm

[11] Patent Number: 4,512,572

[45] Date of Patent: Apr. 23, 1985

[54] MULTI-PURPOSE SPORTS-KIT

[76] Inventor: Wilfried Hamm, Im Wiesengrund 28, 4330 Mulheim-Ruhr, Fed. Rep. of Germany

[21] Appl. No.: 509,350

[22] Filed: Jun. 29, 1983

[30] Foreign Application Priority Data

Nov. 10, 1982 [DE] Fed. Rep. of Germany ... 8231535[U]

[51] Int. Cl.³ .................... A61F 5/00

[52] U.S. Cl. .................... 272/144; 272/145; 128/75

[58] Field of Search .................... 272/144, 134, 145; 128/70-75, 24 R; 5/133, 146

[56] References Cited

U.S. PATENT DOCUMENTS 3,517,397 6/1970 Moore .................... 5/133
3,647,209 3/1972 La Lanne .................... 272/144 X
3,711,878 1/1973 George et al. .................... 5/133
3,752,153 8/1973 Copeland .................... 128/24 R
4,103,681 8/1978 Shanley .................... 128/75 X
4,114,613 9/1978 Kuhn .................... 128/71 X

*Primary Examiner*—Robert A. Hafer
*Assistant Examiner*—Chris Coppens
*Attorney, Agent, or Firm*—McCormick, Paulding & Huber

[57] ABSTRACT

A support structure has laterally spaced ramps alongside a vertical post with a cable connected to a drive system and to a bed, which bed can be moved from near horizontal to vertical and beyond to suspend someone from foot holding devices on the bed. One version has a lost motion detent to permit the user to hang free of the bed. Another version has a pillow on the bed to help support him.

8 Claims, 9 Drawing Figures

MULTI-PURPOSE SPORTS-KIT

The invention is a multi-purpose sports kit which allows a relaxed extension of the body, especially of the spinal column and a strengthening of the abdominal muscles.

There are already known some athlethic implements which e.g. enable the body's relaxed extension by putting the feet into a foothold which is fixed to a horizontal bar.

Entering and climbing down from this foothold is only possible for sporting well-trained people. There is also still a sports-kit on the market, the purpose of which is to strengthen the abdominal muscles. The bed can be vertically inclined in such a way that the foot is higher than the head.

This requires that the user has to straighten up from this position until he can reach his toes with his hands. A sports-kit of this kind is also only useful for athletic people because it is vertically adaptable only in three big steps.

This invention has been made in order to create a multi-purpose sports-kit which can also be used by sportingly untrained people who want to exercise their abdominal muscels and extend their body relaxedly. Additionally it challenges also trained people to their full extent.

The invented kit comprises a bed which is put on rollers whereby the foot is linked to the vertically adjustable sliding carriage of the support. Furthermore an ascending and descending ramp is defined by the lower part of the support.

The footholder is fastened to the articulation between bed and vertically adjustable sliding carriage. The bed is pulled up by an electrical elevating appliance.

In its top position the footholder is so oriented, by the detent of the bed, in such a position that its medial axis is vertical.

With the detent, the rollers at the vertical prolongation of the ramp, the bed, when it is in top-position, may be at an acute angle with respect to the vertical axis of the footholder.

The vertically adjustable sliding carriage, guided in the support is attached to a cable or a chain which is linked to the electric elevating appliance by means of the upper guide pulley.

The following figures will explain the invention in details.

DETAILED DESCRIPTION OF FIGS. 1–4

Figure 1:
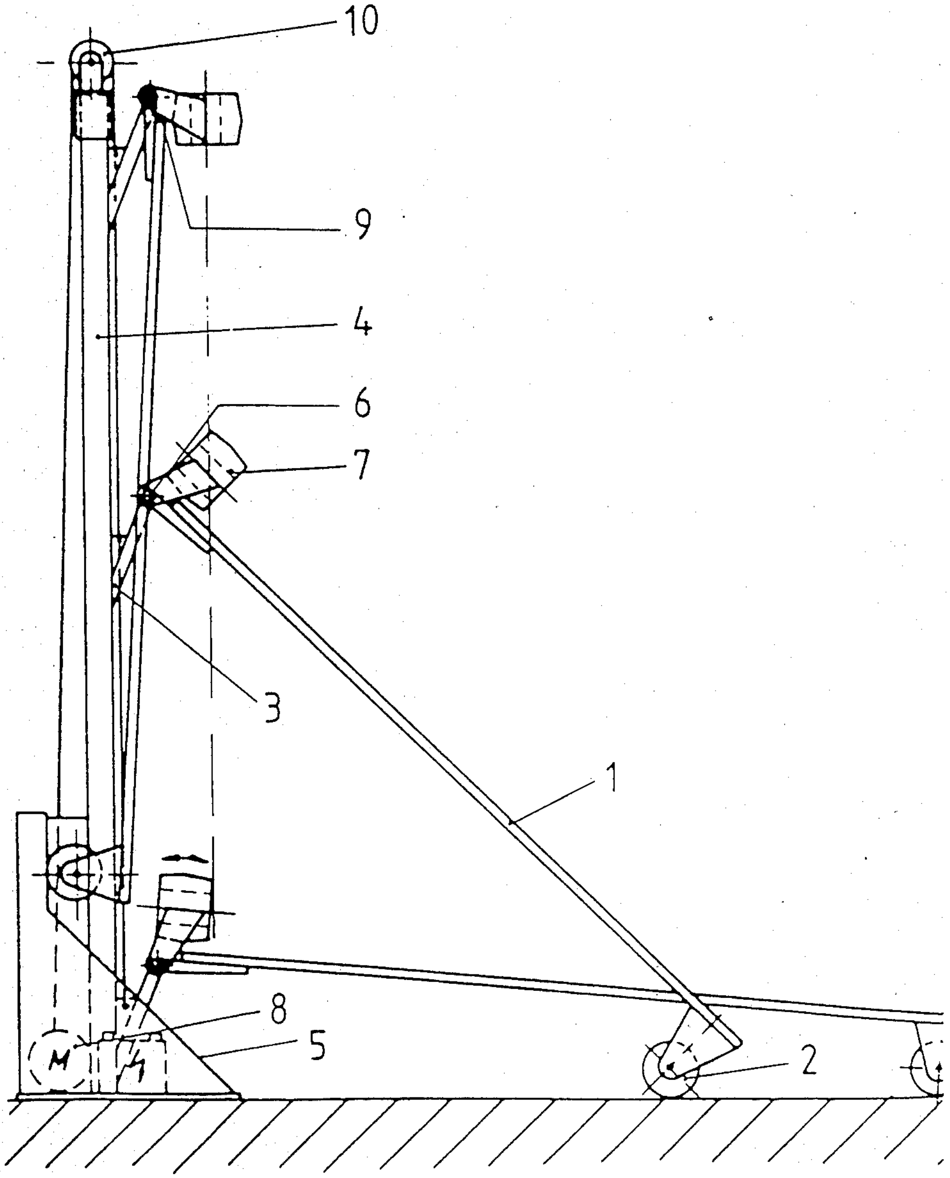
FIG. 1 shows the profile of the whole sports-kit in the two final and in the medium position of the bed.
Figure 2:
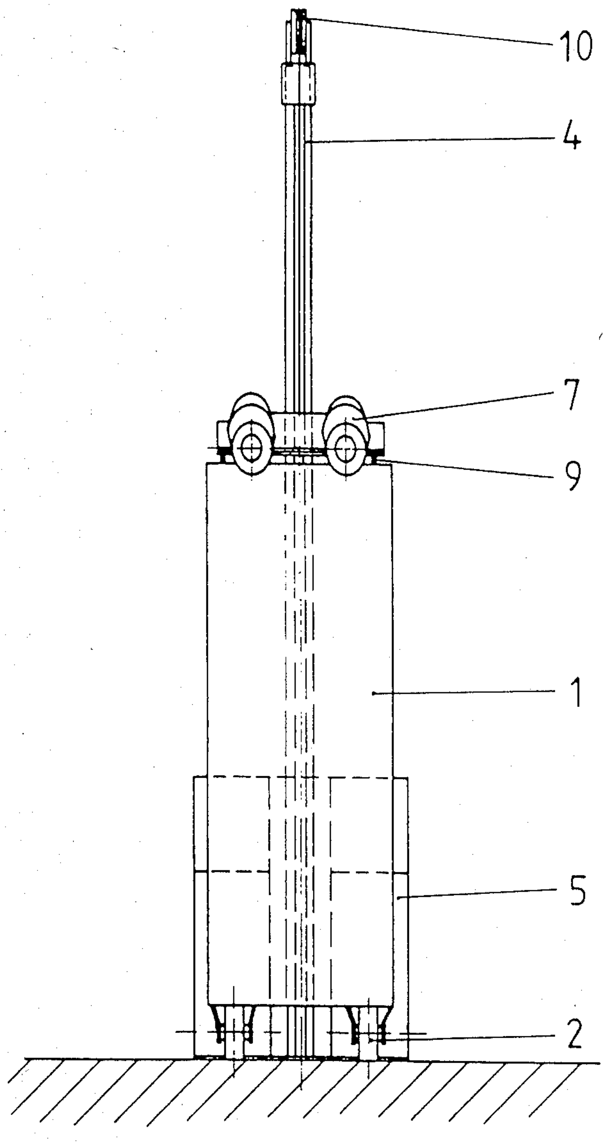
FIG. 2 shows the front view of the appliance whereby the bed is in its medium position.
Figure 3:
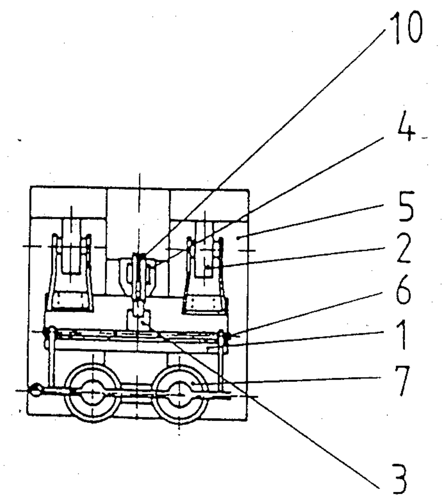
FIG. 3 shows the top view of the kit, the bed is in top-position.
Figure 4:
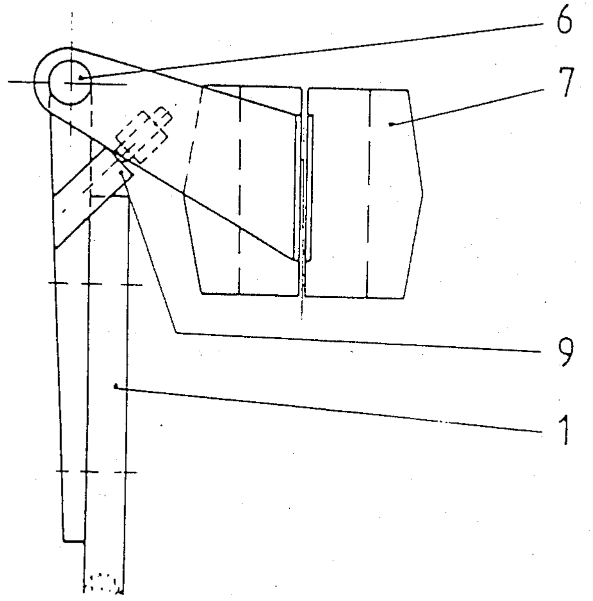
FIG. 4 shows the details of the footholder articulation.
Figure 5:
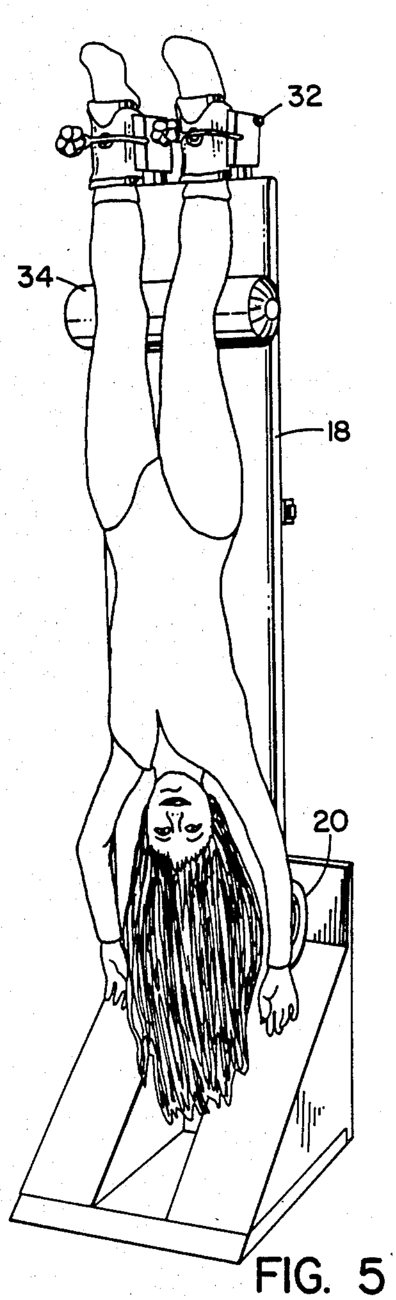
FIG. 5 shows in perspective an alternative version of the apparatus as illustrated in FIGS. 1–4.

Two rollers (2) are fitted below the head of the bed (1). The foot of the bed is pliably linked to the vertically adjustable sliding carriage (3). The movability of the footholder ends when the bed strikes the support. This detent (9) brings the medial axis of the footholder in a vertical position when the bed is in the top position.

The vertically adjustable sliding carriage (3) is guided within the U-profile steel construction of the support (4) by rolls.

A cable or chain is linked to the vertically adjustable sliding carriage by which the latter can be pulled up and down by means of the guide pulley (10) and the electrical elevating appliance (8). The latter can be e.g. cable drum with a low voltage motor and an accumulator.

The elevating appliance can be operated by electric switches, while lying on the bed.

Moreover a security-time-control mechanism can be installed which causes the bed's running down after a certain period of time.

Starting position of the bed is the lower position of the vertically adjustabe sliding carriage. When the bed is horizontal, one lies down after having the feet in the footholder (7).

By actuating the distant switch, the foot of the bed is elevated continuously. This movement can be stopped in every position desired in order to train the abdominal muscles.

While pulling the bed higher, the rollers (2) of the bed will enter the ramp (5). In its top position the bed will not exceed the vertical and will be at an acute angle with the vertically fixed axis of the footholder. The user's body will hang vertically as effected by the weight of the human body which has an effect on the pliably fastened footholder.

Owing to its detent (9) the footholder presses on the also pliably fastened bed, the detent of which is built by the rolls and the vertical-prolongation of the ramp (5). The two detents co-operate with regard to the weight of the human body and therefore they determine the vertical line of the footholder's medium axis and the acute angle of this axis with the bed.

This geometry enables the body to hang free and relaxed and without any touch to the bed.

While the bed runs down the body contacts it when the rolls enter the ramp. Then the bed returns to its horizontal starting position while the user lies down on it.

DETAILED DESCRIPTION OF FIGS. 5–9

In this alternative version, the same general features are present as in the embodiment of FIGS. 1–4, but certain details do differ and will be emphasized in the description to follow.

Somewhat larger rolls or wheels (20, 20) are provided at the head of the bed (18) to facilitate the free travel of the bed during movement across the floor and up the ramps (25, 25) provided in the base.

An electric motor (not shown) drives a cable (16) which passes over a pulley (not shown) at the top of post (14) and is connected to a sliding carriage [similar to the carriage (3) of FIGS. 1–4].

Figure 7:
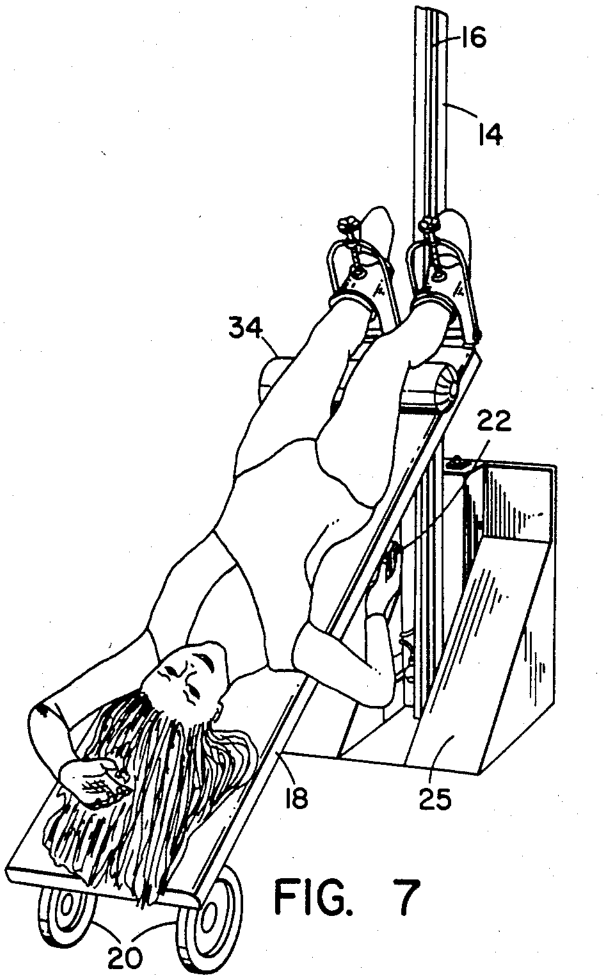
FIG. 7 shows the bed of the FIG. 5 apparatus being elevated by the user by means of the electric switch at the side of the bed.
Figure 8:
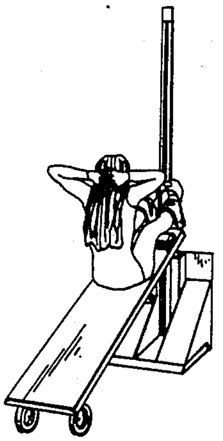
FIG. 8 shows the bed in an inclined position with the user doing a basic exercise thereon.
Figure 9:
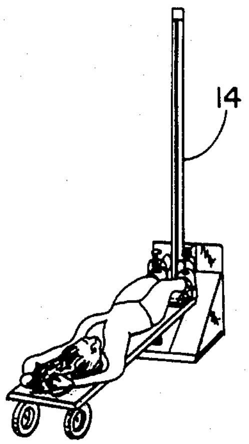
FIG. 9 shows the bed near the horizontal for another type of exercise.
Figure 6:
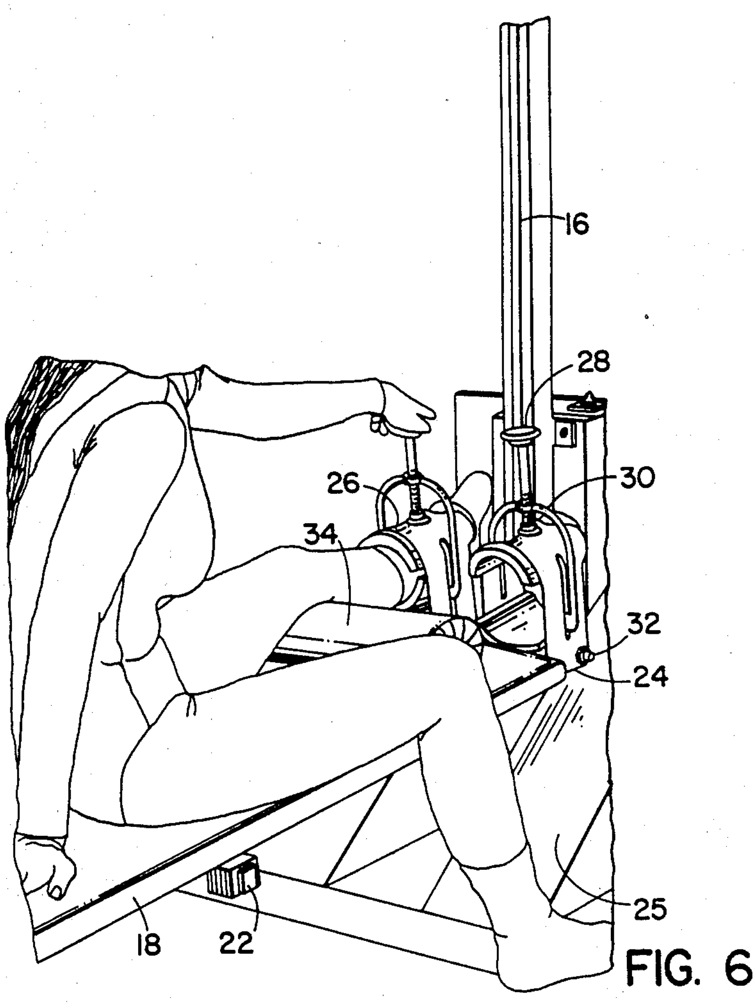
FIG. 6 shows the foot clamping devices of the FIG. 5 apparatus in greater detail.

The motor is controlled [up and down] by one or more switches (22) at the side of the bed (18) as best shown in FIGS. 6 and 7.

The foot clamping devices at the foot of the bed (18) are also shown in detail in FIGS. 6 and 7. Each such device has a base portion (24) and a movable top portion (26) connected to the base by a thumbscrew (28) and a bail (30) such that one can rotate the thumbscrew 28 to move top (26) toward and away from base (24) to clamp one's foot in this foothold device.

These foot clamping devices are preferably mounted in fixed relation to the bed [rather than being movable relative thereto as suggested in the several views of FIG. 1] and the carriage provided in both embodiments has one portion which is slidably received on the post as mentioned previously. Another portion of this carriage 3 comprises a bracket or support arm secured to the carriage at one end to project upwardly and outwardly therefrom [See FIG. 1] and which bracket is pivotally connected to the bed and to the base portions of the footholder devices by a rock shaft (32). In the version shown in FIGS. 1-4 the limited pivotable movement of the foothold devices (7, 7) may be restricted by the detent or stop means (9). In the version of FIGS. 5-9, however, the foot clamping devices (24) do not move relative to the bed (18). In order to avoid any discomfort to the user in the latter version a small pillow (34) is provided on the bed (18) behind the users knees. This pillow will keep the user's legs from locking and will avoid the necessity for the more complex lost motion detent or stop (9) required in the version of FIGS. 1-4.

I claim:

1. An exercising apparatus comprising in combination, a support base adapted to stand on a horizontal floor, said base defining an inclined ramp surface and a vertically upwardly extending post, a carriage slidably mounted on said support post, powered means for raising and lowering said carriage, a bed having one end pivotably mounted to said carriage, rollers at the opposite end of said bed and adapted to roll across the floor adjacent said support, and clamping devices to hold a persons feet at said one end of said bed, said one end when raised in response to raising said carriage causes the rollers to move across the horizontal floor and to ride up said ramp to support the person from said clamping devices so that he is suspended generally vertically in addition to being supported in intermediate inclined positions.

2. The apparatus of claim 1 wherein said bed has a raised pillow portion located behind the knees of a person so clamped in position on said bed by said footholder clamping devices.

3. The apparatus of claim 1 wherein said powered means includes electrical control means for so moving said carriage, said control means including an electric switch on said bed and readily accessible to a person so clamped in position on said bed.

4. The apparatus of claim 1 wherein said footholder clamping devices comprise base portions affixed to said one end of said bed, top portions movably mounted to said base portions and manually movable thumbscrews for moving said top portions relative to said base portions to clamp one's fee while seated on said bed.

5. The apparatus of claim 1 wherein said one end of said bed is pivotably connected to said carriage by a rock shaft provided in association with said footholder clamping devices.

6. The apparatus of claim 1 wherein said powered means includes a cable connected at one end to said carriage, a pulley adjacent the top of said post, and an electric motor connected to the other end of said cable so that said cable extends over said pulley and thereby can raise or lower said carriage in response to said motor's direction of movement.

7. The apparatus of claim 6 wherein said powered means includes electrical control means for so moving said carriage, said control means including an electric switch on said bed and readily accessible to a person so clamped in position on said bed.

8. The apparatus of claim 7 wherein said control means further includes time delay means for causing the bed to return to its down position after a predetermined time.

* * * * *